United States Patent [19]

Thompson et al.

[11] Patent Number: 4,558,067
[45] Date of Patent: Dec. 10, 1985

[54] PHENYLTHIOMETHYL-6-HYDROXY-2,3-DIHYDROBENZO-PYRAN AND ANALOGS THEREOF USEFUL AS ANTI-INFLAMMATORY AGENTS

[75] Inventors: Kathryn L. Thompson, Westfield; Robert A. Zambias, Hoboken; Milton L. Hammond, Edison; Michael N. Chang, Westfield, all of N.J.

[73] Assignee: Merck & Co., Inc., Rahway, N.J.

[21] Appl. No.: 585,070

[22] Filed: Mar. 1, 1984

[51] Int. Cl.$^4$ .................. A01N 43/16; C07D 311/04
[52] U.S. Cl. .................. 514/458; 549/408; 549/409
[58] Field of Search .............. 549/409, 408, 469; 424/284

[56] References Cited
U.S. PATENT DOCUMENTS 4,358,616 11/1982 Wedemeyer ............... 568/45

FOREIGN PATENT DOCUMENTS 551326 5/1977 U.S.S.R. .
556599 11/1977 U.S.S.R. .

OTHER PUBLICATIONS

Nasirov, M. N., (Inst. Khim Prisadok. Baku) Sint. Issled. Biol. Soedin, Tezisy Dokl. Konf. Molodykh Uch. 6th, (1978), 107–8, (Russian).
Chemical Abstract 93:71281y, (1980).
Chemical Abstract 92:76725k, (1980).
Chemical Abstract 83:58283z, (1981).

Primary Examiner—Ethel G. Love
Attorney, Agent, or Firm—Theresa Y. Cheng; Mario A. Monaco

[57] ABSTRACT

Phenylthiomethyl-6-hydroxy-2,3-dihydrobenzopyran and analogs thereof were prepared from an appropriate (6-hydroxy-2,3-dihydro-benzopyran-7-yl) formaldehyde or analog thereof with a substituted thiophenol. These compounds were found to be potent anti-inflammatory agents.

12 Claims, No Drawings

PHENYLTHIOMETHYL-6-HYDROXY-2,3-DIHYDROBENZO-PYRAN AND ANALOGS THEREOF USEFUL AS ANTI-INFLAMMATORY AGENTS

BACKGROUND OF THE INVENTION

The present invention relates to novel substituted 6-hydroxy-2,3-dihydrobenzopyran and analogs thereof useful as anti-inflammatory agents.

It has been observed that the novel compounds of this invention are active in vitro in both the peritoneal macrophage assay and the polymorphonuclear leukocyte assay for general anti-inflammatory activity. Specifically, they are found to be active in vivo in the mouse ear assay for topical anti-inflammatory agents. Furthermore, these compounds tend to be inactivated in vivo after deeper and longer penetration into the body system and are therefore devoid of any significant adverse side effects normally associated with systemic activity.

Recent studies demonstrated that macrophages participate in the development and progression of chronic inflammatory diseases such as rheumatoid arthritis. During the progression of inflammatory conditions, there is generally an appearance and/or presence of macrophages and lymphocytes, especially macrophages and polymorphonuclear leukocytes. Macrophages are known to secrete various products in response to inflammatory stimuli. For example:

(1) Neutral proteases—the destructive peptide bond cleaving enzymes which have been shown to be directly involved in rheumatoid cartilage destruction; and (2) Prostaglandins (PG) (e.g., $E_2$ and $I_2$ by mouse peritoneal macrophages) and other arachidonic acid derivatives derived from both the cyclooxygenase and the lipoxygenase pathways.

These arachidonic acid oxygenation products have been identified as the critical mediators of various acute inflammatory conditions.

Accordingly, pharmacological agents which are capable of inhibiting the formation or the release of a mediator and thereby interfere with the function of macrophages or polymorphonuclear leukocytes may also be effective anti-inflammatory agents. For example, nonsteroidal anti-inflammatory drugs such as indomethacin and clinoril are known cyclooxygenase inhibitors. Through their ability to inhibit the formation of prostaglandins, they have been used for rheumatoid arthritis and osteoarthritis. Other inflammatory diseases such as emphysema, bronchial inflammation, acute respiratory distress syndrome, spondylitis, lupus, gout, and psoriasis may also be treated with these pharmacological agents.

Regarding the topical mouse ear assay, it has been previously established that classical nonsteroidal anti-inflammatory agents such as indomethacin and steroidal anti-inflammatory agents such as dexamethasone are active in this assay.

Another object of this invention is to provide appropriate processes for the preparation of the subject novel compounds.

Still a further object of the present invention is to provide a pharmaceutically acceptable composition containing an effective amount of the active compound for the treatment of various inflammatory conditions.

Finally, it is the ultimate object of this invention to develop a method of treating inflammation via the administration of a therapeutically effective amount of the novel compounds or pharmaceutically acceptable composition thereof to a mammalian species in need of such treatment.

DETAILED DESCRIPTION OF THE INVENTION

A. Scope of the Invention

This invention relates to novel compounds of formula (I) and (II)

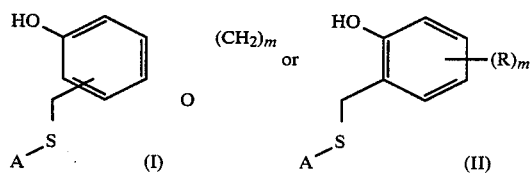

or a pharmaceutically acceptable salt thereof, wherein R is (a) hydroxyloweralkyl especially $C_{1-6}$ hydroxyalkyl such as $-CH_2OH$, $-CH_2CH_2OH$ or

(b) lower alkanoyl;
(c) CN;
(d) halo;
(e) mercaptoloweralkyl especially mercapto $C_{1-6}$ alkyl such as $-CH_2SR^2$ where $R^2$ represents H or loweralkyl,
(f) loweralkylthio especially $C_{1-6}$alkylthio such as $-SCH_3$;
(g) lowerhaloalkyl;
(h) $-COOR^2$;
(i) hydroxycarbonylloweralkyl especially hydroxycarbonyl-$C_{1-6}$ alkyl such as $-CH_2COOH$;
(j) loweralkoxycarbonylloweralkyl especially $C_{1-6}$ alkoxycarbonyl $C_{1-6}$ alkyl such as $-CH_2COO$ t-Bu;
(k) haloloweralkanoyl especially halo $C_{1-6}$ alkanoyl such as trifluoroacetyl;
(l) loweralkoxy especially $C_{1-6}$ alkoxy such as methoxy, ethoxy and propoxy, with the proviso that R cannot be loweralkoxy when A is phenyl; or
(m) loweralkanoyloxyloweralkyl such as $-CH_2OCOCH_3$;

m is an integer ranging from 1 to 4;

A is (a) phenyl substituted with $(R^1)_q$ wherein when there are more than one $R^1$ (i.e., $q > 1$), they can be the same or different from each other and is (1) hydrogen;
(2) halo especially fluoro, chloro or bromo;
(3) loweralkoxy especially $C_{1-6}$ alkoxy, e.g., methoxy, ethoxy, isopropoxy, t-butoxy or cyclohexyloxy, or $-OCH_2O-$;
(4) lower alkylthio especially $C_{1-6}$ alkylthio, or $C_{1-6}$ haloalkylthio e.g., methylthio, ethylthio, trifluoromethylthio or cyclohexylthio;
(5) lower alkyl sulfinyl especially $C_{1-6}$ alkyl sulfinyl, e.g., methyl sulfinyl, i-propyl sulfinyl, and cyclopentyl sulfinyl;
(6) lower alkyl sulfonyl especially $C_{1-6}$ alkyl sulfonyl such as methyl sulfonyl, ethyl sulfonyl and n-butyl sulfonyl;

(7) unsubstituted or substituted phenyl loweralkoxy such as benzyloxy;
(8) loweralkyl especially $C_{1-6}$ alkyl such as methyl, ethyl, propyl, t-butyl, pentyl, benzyl, cyclopropyl, cyclopentyl or cyclohexyl;
(9) loweralkenyl especially $C_{2-6}$ alkenyl, for example, vinyl, allyl, and buten-2-yl;
(10) lower alkanoyl especially $C_{1-6}$ alkanoyl such as formyl, acetyl or i-propanoyl;
(11) haloloweralkyl especially $C_{1-6}$ haloalkyl such as trifluoromethyl;
(12) —COOH or —COO$C_{1-6}$alkyl;
(13) aryl especially phenyl or substituted phenyl, e.g., 4-methoxyphenyl, 2,4-difluorophenyl or 3-chlorophenyl; or
(14) aryloxy especially phenoxy;
(15) cyano;
(16) hydroxyloweralkyl especially hydroxy $C_{1-3}$alkyl such as —CH$_2$OH;
(17) halo loweralkanoyl especially halo$C_{1-6}$ alkanoyl eq. CF$_3$CO;
(18) heteroaryl as defined below; or
(19) loweralkanoyloxy especially acetyloxy;

q is is an integer ranging from 0 to 5;
(b) unsubstituted or substituted heteroaryl, for example:
(1) thienyl;
(2) benzothienyl;
(3) furyl;
(4) benzofuryl;
(5) pyrryl;
(6) indolyl;
(7) thiazolyl;
(8) benzothiazolyl;
(9) thiadiazolyl;
(10) benzothiadiazolyl;
(11) quinolyl;
(12) isoquinolyl;
(13) pyrazinyl;
(14) tetrazolyl; or
(15) triazolyl The heteroaryl above can be substituted with one or more of $R^1$, e.g, $C_{1-6}$ alkyl, $C_{1-6}$ alkanoyl, $C_{1-6}$ haloalkyl, halo, cyano, or hydroxy $C_{1-3}$alkyl. In a preferred embodiment of this invention, the compounds are of formula (II) wherein
R is
(a) COOR$^2$;
(b) loweralkoxy with the provision that when A is phenyl, R cannot be loweralkoxy;
(c) haloloweralkanoyl especially halo $C_{1-6}$ alkanoyl such as CF$_3$CO—;
(d) halo;
(e) loweralkanoyl especially acetyl;
(f) lowerhaloalkyl especially trifluoromethyl;
(g) hydroxyloweralkyl e.g. —CH$_2$OH; or
(h) loweralkanoyloxyloweralkyl;
A is
(a) phenyl substituted with $(R^1)_q$ where $R^1$ and q are as previously described; or
(b) heteroaryl; and
m is 1, 2 or 3

In another preferred embodiment of this invention, the compounds are of formula (I), A is phenyl substituted with $(R^1)_q$ wherein
$R^1$ is
(a) hydrogen;
(b) loweralkoxy;
(c) halo;
(d) lowerhaloalkyl,
(e) loweralkanoyl;
(f) hydroxyloweralkyl; or
(q) CN;

q is 1 or 2; and
m is 1 or 2.

In a more preferred embodiment of the present invention, the compounds are of the following formulae:

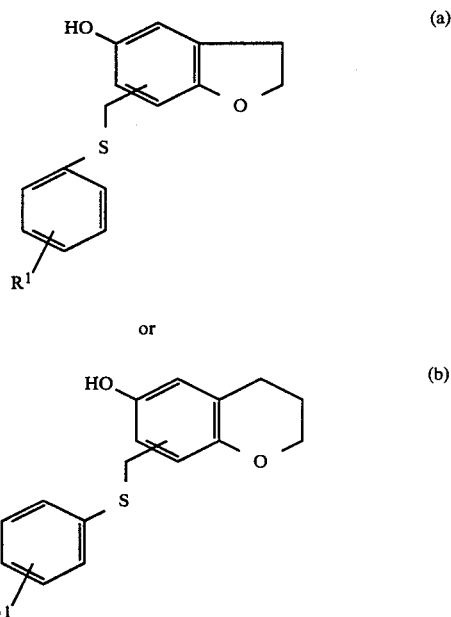

wherein $R^1$ is loweralkanoyl, loweralkanoyloxyloweralkyl, hydroxyloweralkyl or halo.

B. Preparation of the Compounds within the Scope of the Invention:

The novel compounds of the present invention are prepared from the following processes:

Scheme (a) for example:

Step A:

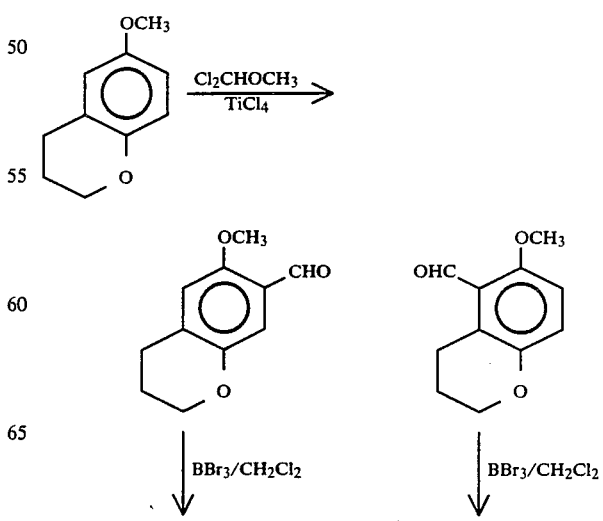

5

-continued

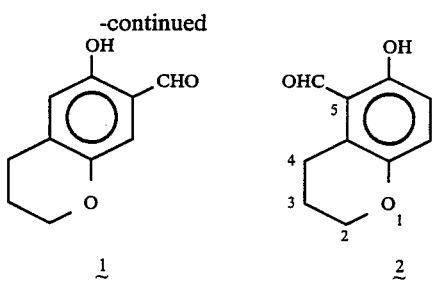

STEP B:

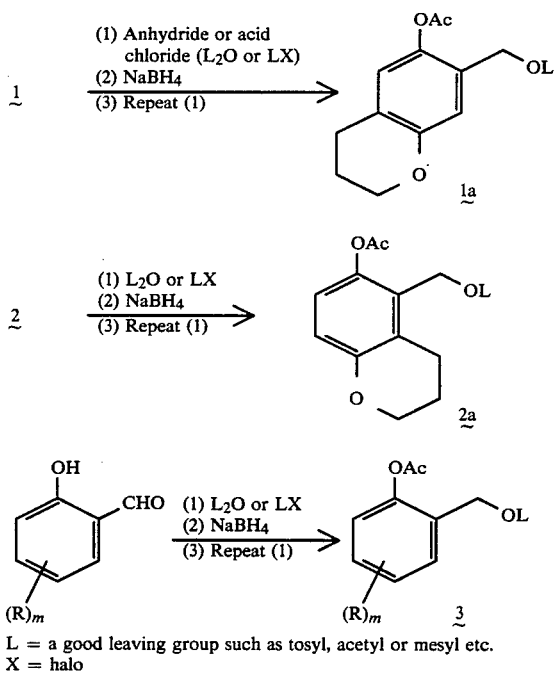

L = a good leaving group such as tosyl, acetyl or mesyl etc.
X = halo

STEP C:

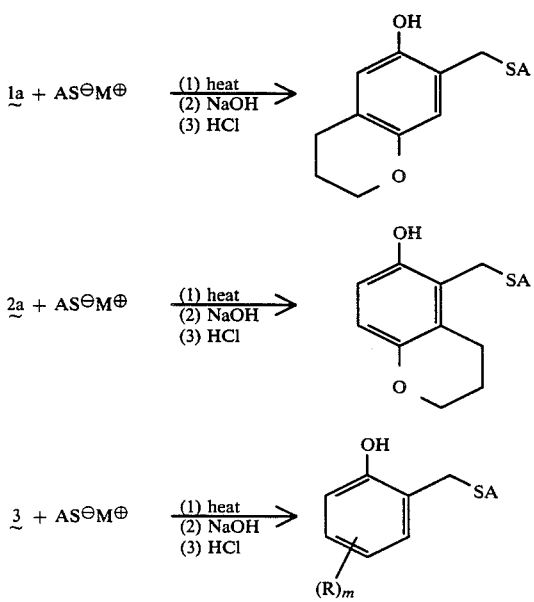

wherein M is an alkali or alkaline earth metal such as sodium, potassium or lithium.

6

C. Utility of the Subject Compounds of the Invention

This invention also relates to a method of treating inflammation in patients in need of such treatment. Generally, a sufficient amount of a compound of formulae (I) or a pharmaceutical composition thereof, particularly an especially preferred compound, is administered to the patient as the active constituent.

For treatment of inflammation, fever or pain, the compounds of the invention are administered topically, by inhalation spray or rectally in dosage unit formulations containing conventional non-toxic pharmaceutically acceptable carriers, adjuvants and vehicles.

The pharmaceutical compositions containing the active ingredient may be in a form suitable for topical use, for example, aqueous or oily solutions or suspensions, dispersible powders or granules, tinctures, topical aerosol emulsions, creams, ointments, jellies, suppositories or the like. Compositions intended for topical use may be prepared according to any method known to the art for the manufacture of pharmaceutical compositions and such compositions may contain one or more active compounds.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules are suitable for the preparation of an aqueous suspension by mixing them with water. They provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth, naturally-occurring phosphatides, for example, soy bean, lecithin, and esters or partial esters derived from fatty acids and hexitol anhydrides, for example, sorbitan mono-oleate, and condensation products of the said partial esters with ethylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sebacate, ethyl carproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.2 mg to 140 mg per kilogram of body weight per day are useful in the treatment of the above-indicated conditions (10 mg to 7 gms per patient per day). For example, inflammation is effectively treated by the administration from about 0.5 to 50 mg of the compound per kilogram of body weight per day (25 mg to 5 gms per patient per day).

The amount of active ingredient that may be combined with the carrier materials to produce a single dosage form will vary depending upon the host treated and the particular mode of administration. Dosage unit forms will generally contain between from about 25 mg to about 1 g of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Set forth below are some illustrative topical formulations containing a selected active compound of the instant invention.

FORMULATION NUMBER 1

Solution (a) Distilled water qs to 100%

Procedure: Dissolve a compound of formula (I) in enough water to make 100%. Filter the solution. Apply to the affected area.

FORMULATION NUMBER 2

Tincture (b)

Alcohol U.S.P.—50%

Water qs to 100%

Procedure: Dissolve a compound of formula (II) in the alcohol. Add sufficient water to make 100%. Filter and apply to affected area.

FORMULATION NUMBER 3

Topical Aerosol (c)

Alcohol U.S.P.—5%

Isopropylmyristate—5%

Conventional halogenated hydrocarbon propellant qs 100% e.g., Freon 11(trichloroflouromethane), Freon 12(dichlorodifluoromethane), Freon 14 (carbon tetrafluoride), Freon C 318 (Octafluorocyclobutane), Freon 114(Cryofluorane), etc.

Procedure: Dissolve a compound of formula (I) in the alcohol and isopropylmyristate. Add sufficient halogenated propellant and introduce into conventional aerosol containers either by pressure or by cold filing. Apply to affected area.

FORMULATION NUMBER 4

Ointment

Petrolatum U.S.P. qs to 100%

Procedure: Heat the petrolatum to 60° C. Add a compound of formula (I) and stir until thoroughly dispersed. Cool to room temperature. Apply to affected area.

EXAMPLE 1

6-Methoxy-3,4-dihydrobenzopyran-5-carboxaldehyde, 6-methoxy-3,4-dihydrobenzopyran-7-carboxaldehyde and 6-methoxy-3,4-dihydrobenzopyran-8-carboxaldehyde A solution of 6-methoxy-3,4-dihydrobenzopyran (133.0 g, 811 mmol) in dry methylene chloride (1850 mL) was cooled to 5° under nitrogen and titanium tetrachloride (145 mL, 250.2 g, 1319 mmol) was added dropwise over 15 minutes. Upon completion of this addition dichloromethylmethylether (60 mL, 76.26 g, 663 mmol) was added dropwise over 45 minutes. A slight exotherm was observed during the addition (reaction temperature=16°). The cooling bath was removed and the mixture allowed to stir for three hours, then quenched by the dropwise addition of water (300 mL). The resulting mixture was poured into water (1000 mL), the layers separated, and the organic layer washed with water (1000 mL). The combined aqueous layers were back extracted with methylene chloride (500 mL), then the combined organic extracts were washed with brine ($2 \times 1000$ mL), dried ($Na_2SO_4$) and concentrated to a dark oil (152.0 g). Purification by preparative HPLC (Waters Prep 500, 9:1 hexane:ethylacetate as eluant) afforded, in order of elution, 6-methoxy-3,4-dihydrobenzopyran-5-carboxaldehyde (32.52 g, 20.9%) m.p. 52°-54°, 6-methoxy-3,4-dihydrobenzopyran-8-carboxaldehyde (31.83 g, 20.4%) m.p. 69°-71°, and 6-methoxy-3,4-dihydrobenzopyran-7-carboxaldehyde (31.49 g, 20.2%) m.p. 57°-59°.

EXAMPLE 2

6-Hydroxy-3,4-dihydrobenzopyran-7-carboxaldehyde

A solution of 6-methoxy-3,4-dihydrobenzopyran-7-carboxaldehyde (30.00 g, 156 mmol) in dry methylene chloride (625 mL) under nitrogen was cooled to an internal temperature of $-67°$. A solution of boron tribromide (1M in methylene chloride, 67.5 mL, 67.5 mmol) was added dropwise. The cooling bath was removed and the mixture allowed to stir under nitrogen for three hours. The reaction was then quenched by the dropwise addition of methanol (75 mL) and the resulting mixture poured into saturated aqueous sodium chloride (1200 mL). The layers were separated and the organic extract washed with saturated sodium chloride (600 mL), dried (Na2SO4) and concentrated to a dark solid (31.0 g). Purification by preparative HPLC (Waters Prep 500, 9:1 hexane:ethyl acetate as eluant) afforded 6-hydroxy-3,4-dihydrobenzopyran-7-carboxaldehyde (18.80 g, 67.6%), m.p. 97°–100°.

EXAMPLE 3

6-Acetoxy-3,4-dihydrobenzopyran-7-carboxaldehyde

To a solution of 6-methoxy-3,4-dihydrobenzopyran-7-carboxaldehyde (5.00 g, 28.1 mmol) in pyridine (15.0 mL) was added acetic anhydride (3.5 mL, 31.1 mmol) and the mixture allowed to stir at room temperature for 4 hours then poured into ice water (300 mL). The product which precipitated was collected by filtration, washed with water (75 mL) and air dried to afford 6-acetoxy-3,4-dihydrobenzopyran, (5.86 gm, 94.5%), m.p. 76°–77°.

EXAMPLE 4

6-Acetoxy-7-hydroxymethyl-3,4-dihydrobenzopyran acetate

To a suspension of sodium borohydride (985 mg, 26.1 mmol) in ethyl acetate (55 mL) containing a small amount of absolute ethanol (0.2 mL) at 5° C. was added a solution of 6-acetoxy-3,4-dihydrobenzopyran-7-carboxaldehyde (5.68 g, 25.8 mmol) in ethyl acetate (55 mL) dropwise. Ethanol (4 mL) was added and the mixture allowed to warm to room temperature and stir for one hour. The reaction was quenched by the addition of 10% acetic acid (50 mL, dropwise) and the layers separated. The organic layer was washed sequentially with 7% NaHCO3 (3×100 mL) and water (100 mL), dried (Na2SO4), and concentrated to afford a thick yellow oil (5.35 g). The material was taken up in pyridine (15 mL), acetic anhydride (35 mL) was added, and the mixture heated to reflux for ten minutes. Upon cooling, the mixture was poured into ice water and the mixture extracted with ethyl acetate (100 mL). The organic extract was washed sequentially with 2.5N hydrochloric acid (100 mL), 7% NaHCO3 (2×100 mL), and brine (100 mL), dried (Na2SO4) and concentrated to an oil. The crude product was purified by preparative HPLC (10% ethyl acetate/hexane as eluant) to afford 6-acetoxy-7-hydroxymethyl-3,4-dihydrobenzopyran acetate (3.89 g) as a pale yellow oil.

EXAMPLE 5

6-Hydroxy-7-(2-hydroxymethylphenyl)thiomethyl-3,4-dihydrobenzopyran

To a solution of o-mercaptobenzylalcohol (289 mg, 2.06 mmol) in dry dimethylformamide (3 mL) was added sodium hydride (60% dispersion in mineral oil, 83 mg, 2.07 mmol) portionwise and the mixture allowed to stir for 30 minutes. To the resulting solution was added dropwise a solution of 6-acetoxy-7-hydroxymethyl-3,4-dihydrobenzopyran acetate (543 mg, 2.06 mmol) in dry dimethylformamide and the mixture allowed to stir at room temperature under nitrogen for three hours, heated to 50° for 30 minutes, then allowed to cool and stir overnight. The reaction was quenched with 2.5N sodium hydroxide (2 mL) and after stirring for 30 minutes, the mixture was poured into water (75 mL). The aqueous mixture was neutralized with 2N hydrochloric acid (2.5 mL), extracted with ether (2×100 mL) and the ether extract washed with brine (3×100 mL), dried (Na2SO4) and concentrated. The crude product was purified by preparative HPLC (2:1 hexane/ethyl acetate as eluant) to afford 6-hydroxy-7-(2-hydroxymethylphenyl)thiomethyl-3,4-dihydrobenzopyran as a pale off-white solid, m.p. 140°–141° C.

EXAMPLE 6

6-Hydroxy-7-(4-acetylphenyl)thiomethyl-3,4-dihydrobenzopyran

To a solution of 6-acetoxy-7-hydroxymethyl-3,4-dihydrobenzopyran acetate (1.00 g, 3.78 mmol) in dry dimethylformamide (5 mL) was added a solution of potassium p-acetylthiophenoxide (720 mg, 3.8 mmol) in dimethylformamide (5 mL). The mixture was heated at 50° C. for 2.25 hours, then poured into ice water (75 mL). Sodium hydroxide (10% aqueous, 20 mL) was added, then mixture allowed to stir for 30 minutes, then acidified with 2N hydrochloric acid and extracted with ethyl acetate (3×50 mL). The combined extracts were washed with 7% NaHCO3, and brine (2x), dried (Na2SO4) and concentrated. The crude product was purified by preparative HPLC (30% ethyl acetate hexane as eluant and recrystallized from ethyl acetate hexane to afford 6-hydroxy-7-(4-acetylphenyl)thiomethyl-3, 4-dihydrobenzopyran as a white solid (172 mg), m.p. 192°–193° C.

EXAMPLE 7

2-(2-Hydroxy-5-methoxybenzylthio)thiophene

To a suspension of 1.38 g (0.057 moles) Mg in 100 mL anhydrous ether was added 12.0 g (0.057 moles) 2-iodothiophene and the mixture was heated at reflux until the metal dissolved. The solution was cooled to 0°, 1.85 g (0.057 moles) of dry sulfur was added, and the mixture was heated at reflux for 1 hour. A solution of 5.80 g (0.0235 moles) of 1-acetoxy-2-acetoxymethyl-4-methoxybenzene in 25 mL dry tetrahydrofuran was added and the solution was heated at reflux for 1 hour.

The mixture was partitioned between ether and water, washed with K2CO3, NaCl and dried over Na2SO4. The residue (14 g) was chromatographed on silica (15% ethyl acetate-hexane) to afford 4.0 g of a yellow oil that crystallized from 3:1 hexane-methylene chloride to yield 1.85 g of white needles (28%), m.p. 84°.

EXAMPLE 8

2-(2-Hydroxy-3-methoxybenzylthio)thiophene

To a suspension of 0.360 g (14.8 mmol) Mg in 30 mL anhydrous ether was added 3.10 g (14.8 mmol) 2-iodothiophene and the mixture was heated at reflux until the metal dissolved. The solution was cooled to 0°, then 0.480 g (15.0 mmol) sulfur was added, and the mixture was heated at reflux for 1 hour. A solution of 1.50 g (6.10 mmol) of 2-acetoxy-1-acetoxymethyl-3-methoxybenzene in 5 mL dry tetrahydrofuran was added and the solution was heated at reflux for 1 hour.

The mixture was partitioned between ether and water, and the ether layer was washed with K2CO3, NaCl and dried over Na2SO4. The residue was chromatographed on silica (15% ethyl acetate-hexane) and crystallized from petroleum ether-toluene to afford 0.980 g (47%) of white needles, m.p. 50°–51° C.

What is claimed is:

1. A compound of formula (I)

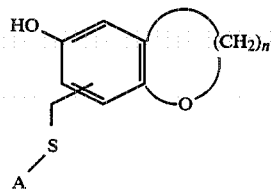 (I)

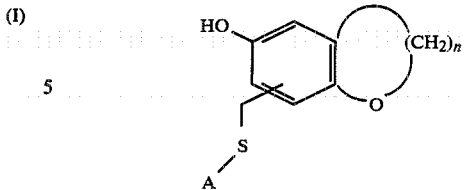 (I)

or a pharmaceutically acceptable salt thereof wherein A is
(a) phenyl substituted with $(R^1)_q$ wherein when there are more than one $R^1$ ($q<1$) and $R^1$ can be the same or different from each other and is
  (1) hydrogen;
  (2) halo;
  (3) loweralkoxy;
  (4) lower alkylthio;
  (5) lower alkyl sulfinyl;
  (6) lower alkyl sulfonyl;
  (7) unsubstituted or substituted phenyl loweralkoxy;
  (8) loweralkyl;
  (9) loweralkenyl;
  (10) lower alkanoyl;
  (11) haloloweralkyl;
  (12) —COOH;
  (13) aryl;
  (14) aryloxy;
  (15) cyano;
  (16) hydroxyloweralkyl;
  (17) halo loweralkanoyl; or
  (18) loweralkanoyloxy;
q is 0 to 5; and
n is 3.

2. The compound of formula (I) according to claim 1 wherein:
A is phenyl substituted with $(R^1)_q$ wherein $R^1$ is
  (a) hydrogen;
  (b) loweralkoxy;
  (c) halo;
  (d) lowerhaloalkyl;
  (e) loweralkanoyl;
  (f) hydroxyloweralkyl; or
  (q) loweralkanoyloxyloweralkyl; and
q is 1 or 2.

3. The compound of claim 1 having formula:

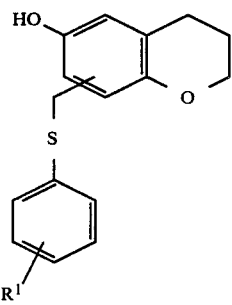

wherein $R^1$ is loweralkanoyl, loweralkanoyloxyloweralkyl, or hydroxyloweralkyl.

4. A pharmaceutical composition for treating topical inflammation comprising a pharmaceutical carrier and an anti-inflammatory effective amount of a compound of formula (I)

or a pharmaceutically acceptable salt thereof wherein A is
(a) phenyl substituted with $(R^1)_q$ wherein when there are more than one $R^1$ ($q>1$) and $R^1$ can be the same or different from each other and is
  (1) hydrogen;
  (2) halo;
  (3) loweralkoxy;
  (4) lower alkylthio;
  (5) lower alkyl sulfinyl;
  (6) lower alkyl sulfonyl;
  (7) unsubstituted or substituted phenyl loweralkoxy;
  (8) loweralkyl;
  (9) loweralkenyl;
  (10) lower alkanoyl;
  (11) haloloweralkyl;
  (12) —COOH;
  (13) aryl;
  (14) aryloxy;
  (15) cyano;
  (16) hydroxyloweralkyl;
  (17) halo loweralkanoyl; or
  (18) loweralkanoyloxy;
q is 0 to 5; and
n is 3.

5. The pharmaceutical composition of claim 4 wherein:
A is phenyl substituted with $(R^1)_q$ wherein $R^1$ is
  (a) hydrogen;
  (b) loweralkoxy;
  (c) halo;
  (d) lowerhaloalkyl,
  (e) loweralkanoyl;
  (f) hydroxyloweralkyl; or
  (q) loweralkanoyloxyloweralkyl; and
q is 1 or 2.

6. The pharmaceutical composition of claim 4 wherein the active compound is of formula:

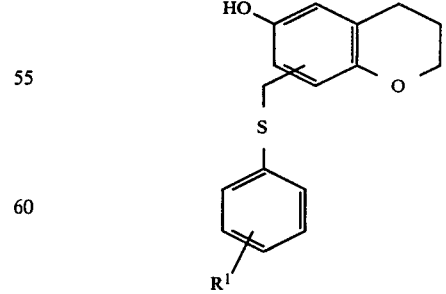

wherein $R^1$ is loweralkanoyl, loweralkanoyloxyloweralkyl, or hydroxyloweralkyl.

7. A method of treating or decreasing topical inflammation comprising the administration to a mammalian species in need of such treatment a anti-inflammatory effective amount of a compound of formula I

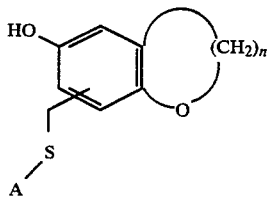

or a pharmaceutically acceptable salt thereof wherein A is
  (a) phenyl substituted with $(R^1)_q$ wherein when there are more than one $R^1$ (q>1) and $R^1$ can be the same or different from each other and is
    (1) hydrogen;
    (2) halo;
    (3) loweralkoxy;
    (4) lower alkylthio;
    (5) lower alkyl sulfinyl;
    (6) lower alkyl sulfonyl;
    (7) unsubstituted or substituted phenyl loweralkoxy;
    (8) loweralkyl;
    (9) loweralkenyl;
    (10) lower alkanoyl;
    (11) haloloweralkyl;
    (12) —COOH;
    (13) aryl;
    (14) aryloxy;
    (15) cyano;
    (16) hydroxyloweralkyl;
    (17) halo loweralkanoyl; or
    (18) loweralkanoyloxy;
q is 0 to 5; and
n is 3.

8. The method of claim 7 wherein:
A is phenyl substituted with $(R^1)_q$ wherein $R^1$ is
  (a) hydrogen;
  (b) loweralkoxy;
  (c) halo;
  (d) lowerhaloalkyl;
  (e) loweralkanoyl;
  (f) hydroxyloweralkyl; or
  (q) loweralkanoyloxyloweralkyl; and
q is 1 or 2.

9. The method of claim 7 wherein the active compound is of formula:

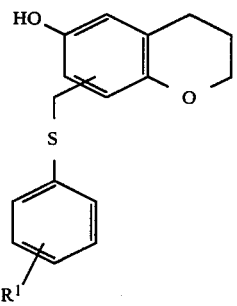

wherein $R^1$ is loweralkanoyl, loweralkanoyloxyloweralkyl, or hydroxyloweralkyl.

10. The compound of claim 1 which is 6-hydroxy-7-(2-hydroxymethylphenyl)thiomethyl-3,4-dihydrobenzopyran.

11. The composition of claim 4 wherein the active compound is 6-hydroxy-7-(2-hydroxymethylphenyl)thiomethyl-3,4-dihydrobenzopyran.

12. The method of claim 7 wherein the active compound is 6-hydroxy-7-(2-hydroxymethylphenyl)thiomethyl-3,4-dihydrobenzopyran.

* * * * *